United States Patent
Niemöller et al.

(10) Patent No.: US 12,181,475 B2
(45) Date of Patent: *Dec. 31, 2024

(54) REAGENTS FOR DETECTION OF CHIMERIC ANTIGEN RECEPTOR CELLS

(71) Applicant: Miltenyi Biotec B.V. & Co. KG, Bergisch Gladbach (DE)

(72) Inventors: Michaela Niemöller, Bergisch Gladbach (DE); Jonathan Fauerbach, Rösrath (DE); Christian Dose, Kürten (DE); Anne Richter, Cologne (DE); Tina Borke, Bergisch Gladbach (DE)

(73) Assignee: Miltenyi Biotec B.V. &Co.KG, Bergisch Gladbach (DE)

( * ) Notice: Subject to any disclaimer, the term of this patent is extended or adjusted under 35 U.S.C. 154(b) by 708 days.

This patent is subject to a terminal disclaimer.

(21) Appl. No.: 17/226,202

(22) Filed: Apr. 9, 2021

(65) Prior Publication Data

US 2021/0373017 A1  Dec. 2, 2021

(30) Foreign Application Priority Data

May 27, 2020  (EP) .................... 20176690

(51) Int. Cl.
*C07K 1/113* (2006.01)
*G01N 33/569* (2006.01)

(52) U.S. Cl.
CPC .............. *G01N 33/56966* (2013.01)

(58) Field of Classification Search
None
See application file for complete search history.

(56) References Cited

FOREIGN PATENT DOCUMENTS

EP   3 211 421 A1   8/2017

OTHER PUBLICATIONS

Au et al 2018 ACS Nano 12: 1544-1563 (Year: 2018).*
Moyer et al. "Engineered immunogen binding to alum adjuvant" Nature Medicine, Nature Pub, vol. 26, No. 3, Feb. 17, 2020.
Kim et al, "Biomedical Applications of copper click-free chemistry," Chemical Science, vol. 10, No. 34, Aug. 28, 2019.

* cited by examiner

*Primary Examiner* — Michael D Pak
(74) *Attorney, Agent, or Firm* — Jaquelin K. Spong

(57) ABSTRACT

The invention is directed to a method for preparing a detection reagent for CAR expressing cells according to general formula (I)

$$(X-S)_m-D \qquad (I)$$

wherein D is a detection moiety, S a spacer unit and X a polypeptide comprising 10 to 80 amino acids and a $N_3$ group, which binds to the antigen binding domain of a chimeric antigen receptor of a cell and m=4-200, characterized in reacting p detection moieties D with a spacer S according to general formula (II)

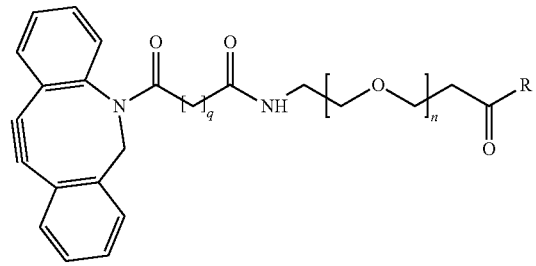

(II)

wherein R is a leaving group, q=1 to 5, and n=4 to 200 and p is 4-250
thereby forming modified detection moiety $S_p$-D and reacting the modified detection moiety $S_p$-D with a plurality of polypeptides X to yield $(X-S)_m$-D.

8 Claims, 8 Drawing Sheets

Specification includes a Sequence Listing.

REAGENTS FOR DETECTION OF CHIMERIC ANTIGEN RECEPTOR CELLS

CROSS REFERENCE TO RELATED APPLICATIONS

This US nonprovisional Patent Application claims priority to EP20176690.4 filed in European Patent Office on May 27, 2020. This priority application is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

The present invention relates to a method and a reagent for detection of chimeric antigen receptor carrying cells (CAR cells).

Chimeric Antigen Receptor (CAR) cells are promising technology and platform in cancer therapy since they can be engineered based on the patient's immune system and according to the specific type of cancer and patient's needs.

The fast development of chimeric antigen receptor (CAR) cells into innovative cell therapies brought along a need to develop adequate detection reagents and methods for their qualitative and quantitative analysis. For example, EP15196309.7 discloses the reprogramming of hematopoietic stem cells by a viral vector specific for the targeted cancer cells.

Given that CAR cells are not stable cell lines, the expression levels of the CAR moiety on the cell surface can be highly variable and dependent on the type of cell (e.g. T cells, B cells, NK cells, DC cells, etc) as well as the CAR moiety being expressed on the cell surface. Thus, it is common for CAR cells to show a wide distribution of CAR expression (from very low to very high) within a certain population. Plus the CAR expression levels could change over a variety of factors such as internalization upon CAR activation or cell passage over time, among others, stressing the need for reliable yet flexible detection methods for CAR cells.

Moreover, since CAR cells are mainly engineered for therapeutic applications, they need to be analyzed in complex biological samples (e.g. whole blood) where they represent but only a very small percentage or fraction of all cells (e.g. between 0.01-0.5%). Hence specificity and sensitivity are crucial topics when dealing with the development of CAR detection reagents.

In this respect, EP3620464A1 discloses a generic detection reagent for CAR T cells based on CD20 receptors.

Altogether, developing a CAR detection reagent which can be adaptable for any type of CAR cell, with enough sensitivity (i.e. brightness) but without compromising selectivity (i.e. unspecific staining, or background staining) is both a real challenge and a burning need for the success and proper analysis of new therapies.

SUMMARY

The present invention is directed to a method to prepare a detection reagent for CD20 CAR expressing cells based on a specific multimerization strategy of an engineered peptide (with high affinity for the anti-CD20 antigen receptor unit on anti-CD20 CAR cells, herein referred to as 'CD20 peptide') and its conjugation to a detection moiety (e.g. fluorescent PE protein) via SPAAC chemistry using DBCO activated PE and $N_3$-terminated CD20 peptide.

Object of the invention is a Method for preparing a detection reagent for CAR expressing cells according to general formula (I)

$$(X\text{-}S)_m\text{-}D \quad (I)$$

wherein D is a detection moiety, S a spacer unit, m=4-200 and X is a polypeptide comprising 10 to 80 amino acids and a $N_3$ group wherein X binds to the antigen binding domain of a chimeric antigen receptor of a cell, characterized in reacting p detection moieties D with a spacer S according to general formula (II)

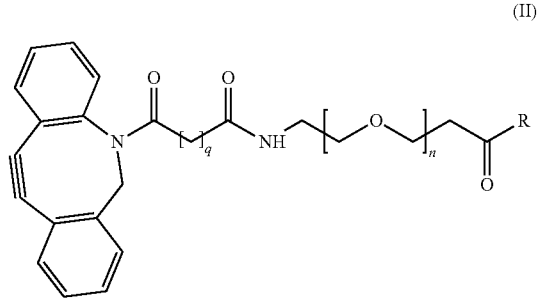

(II)

wherein R is a leaving group, q=1 to 5, and n=4 to 200 and p is 4-250;

thereby forming modified detection moiety $S_p$-D and reacting the modified detection moiety $S_p$-D with a plurality of polypeptides X to yield $(X\text{-}S)_m$-D.

It should be noted that although it is desired to couple all S units of the modified detection moiety $S_p$-D with polypeptides X to obtain the target reagent $(X\text{-}S)_p$-D (i.e. p=m), this might not be always achieved. In praxis, only a part of the polypeptides X are effectively coupled with $S_p$-D which results in reagents having the general formula I $(X\text{-}S)_m$-D. The amount of S units not reacting with X is usually in a range of 0-10% of p; accordingly p>=m with p is 4-220. FIG. 3 shows this variant of the invention.

It is another object of the invention to provide a method for detecting cells expressing an antigen binding domain of a chimeric antigen receptor (CAR), wherein a detection reagent obtained with the method according to the invention is provided to a sample of cells and the cells having an antigen binding domain of a chimeric antigen receptor (CAR) binding the detection reagent are detected via the detection moiety of the detection reagent.

Yet another object of the invention is a detection reagent for CAR expressing cells according to general formula (III)

$$\left(X-N\underset{N}{\overset{N}{\diagdown}}\underset{}{\overset{}{\diagup}}\underbrace{\phantom{XXXX}}_{}N\underset{O}{\overset{O}{\diagdown}}\underset{q}{\overset{}{\diagup}}NH\underset{}{\overset{}{\diagdown}}O\underset{n}{\overset{}{\diagup}}NH\right)_m D \quad (III)$$

with m=4-200, q=1 to 5 and n=4 to 200
wherein X is a polypeptide comprising 10 to 80 amino acids and D is a detection moiety and
wherein X binds to the antigen binding domain of a chimeric antigen receptor of a cell.

Definitions

The term "Chimeric antigen receptor" or "CAR" refers to engineered receptors, which are grafted onto cells. In general, a CAR comprises an extracellular domain (extracellular part) comprising the antigen binding domain, a transmembrane domain and an intracellular signaling domain.

The antigen binding domain of the CAR targets specific antigens. The targeting regions may comprise full length heavy chain, Fab fragments, scFvs, divalent single chain antibodies or diabodies, each of which are specific to the target antigen. The antigen binding domain can be derived from the same species or a different species for or in which the CAR will be used in.

The extracellular spacer or hinge region of a CAR is located between its antigen binding domain and transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions of antibodies, accessory proteins, artificial spacer sequences or combinations thereof. Examples of extracellular spacer domains include but are not limited to CD8 alpha hinge.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof.

The term "antigen" refers to a molecular entity that may be soluble or cell membrane bound in particular but not restricted to molecular entities that can be recognized by means of the adaptive immune system including but not restricted to antibodies or TCRs, or engineered molecules including but not restricted to transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The terms "specifically binds" or "specific for" with respect to an antigen-binding domain of an antibody, of a fragment thereof or of a CAR refers to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

DETAILED DESCRIPTION OF THE INVENTION

Figure 1:
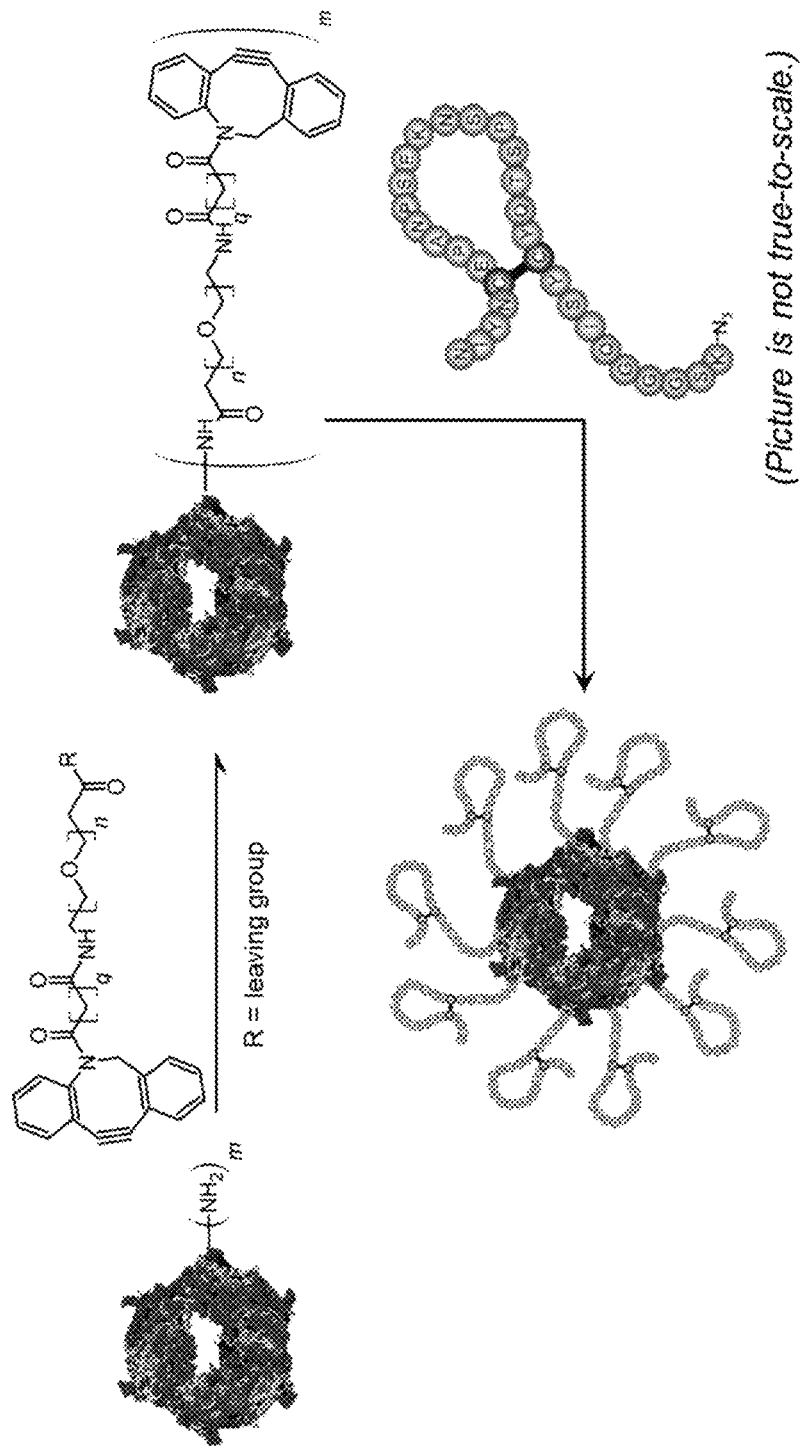
FIG. 1 shows the method of the invention
Figure 2:
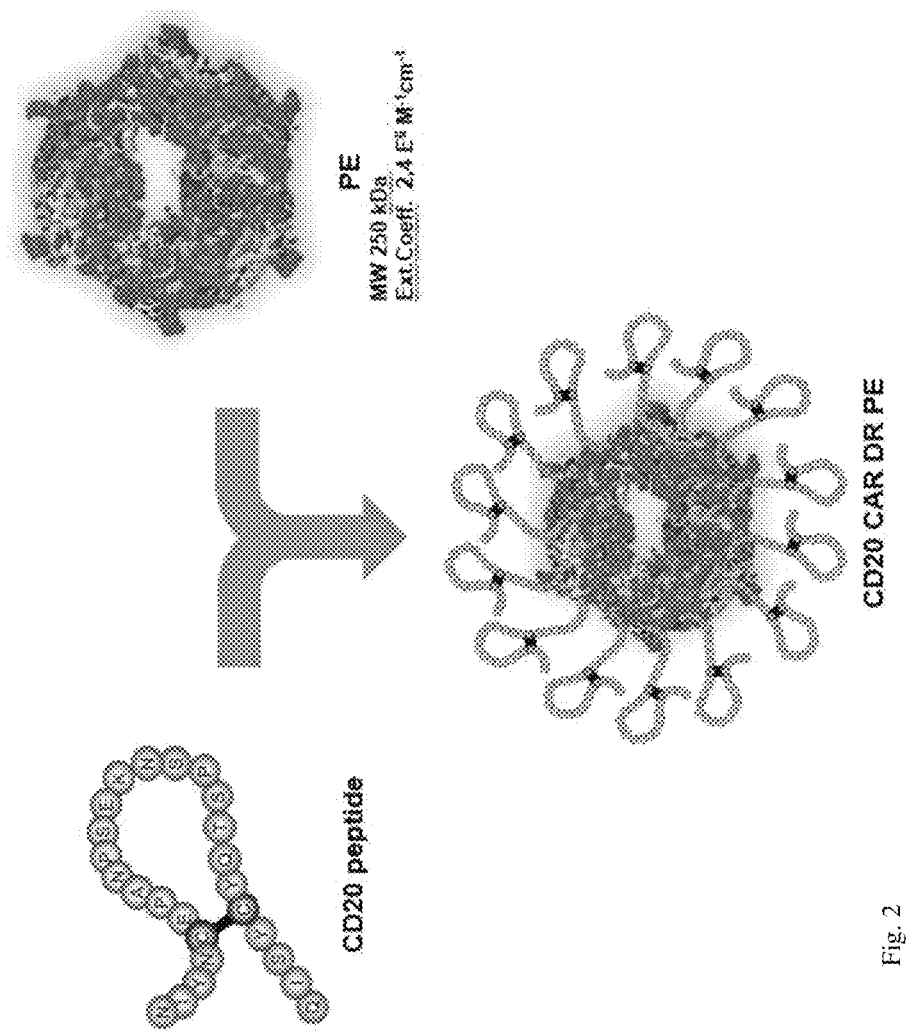
FIG. 2 shows coupling reaction to obtain the reagent $(X-S)_m$-D (I)
Figure 3:
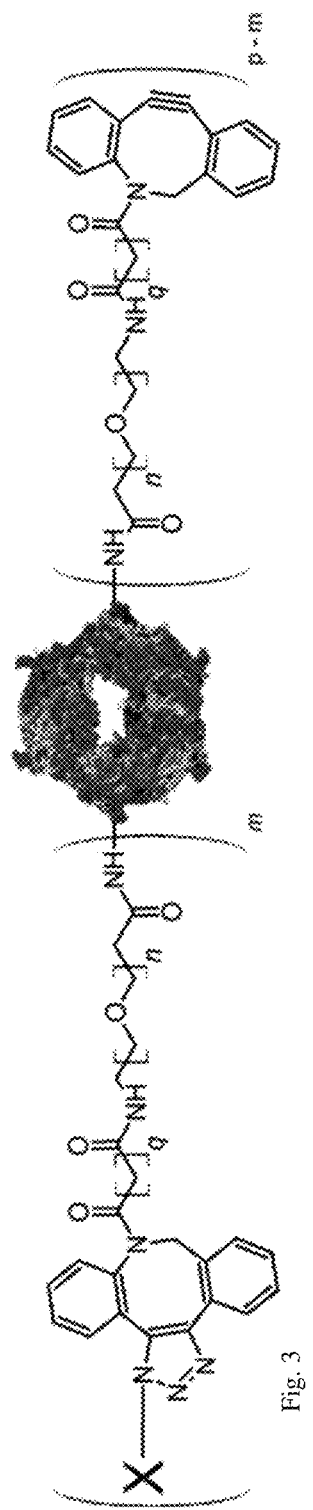
FIG. 3 shows a variant of the reagent $(X-S)_p$-D (I) with unreacted spacer groups still present

Cells with chimeric antigen receptor (CAR), comprising an extracellular part, at least one intracellular signaling domain, and at least one transmembrane domain are known and for example disclosed in WO2014127261A1, WO2015017214A1, WO2015090229A1, WO2015142661A1 and WO2015150771A1.

The method of the invention enables the detection of cells expressing a chimeric antigen receptor (CAR). Preferably such cells are T-cells or subsets of T cells, e.g. naive, stem-cell memory, effector memory, central memory or effector T cells, Natural Killer (NK)-cells or NK-cell subsets, e.g. NK-T cells, or other immune cells.

Polypeptide X

In the method of the invention, polypeptide X reacts via a $N_3$ group, preferable an $N_3$ group provided to the amino acid on the C terminus of polypeptide X, with spacer S.

Polypeptide X comprises 10 to 80 amino acids, preferable 15 to 30 amino acids.

Preferable, at least two amino acids of polypeptide X are connected by at least one disulfide group. Preferable, polypeptide X is an extracellular sequence of CD20.

For example, polypeptide X may have a sequence of amino acids of CEPANPSEKNSPSTQYC (Seq ID 1) or NIYNCEPANPSEKNSPSTQYCYSIQ (Seq ID 2), wherein the amino acids C are connected by a disulfide bond and the amino acid on the C terminus is provided with a $N_3$ group In a preferred embodiment, polypeptide X is provided with an extension of an oligopeptide of 2 to 10 amino acids to the C terminus of the polypeptide X. Most preferred are extensions by oligopeptides having a sequence of amino acids of GGGSK (Seq ID 3). For example, polypeptide X with the sequence NIYNCEPANPSEKNSPSTQYCYSIQ (Seq ID 2) can be extended to sequence NIYNCEPANPSEKNSPSTQYCYSIQGGGSK (Seq ID 4) wherein K as C terminus is provided with a $N_3$ group.

A person skilled in the art will realize that these sequences can be altered to a certain extend without substantially losing specificity. In variants of the present invention, the disclosed sequences of amino acids may have some amino acids deleted, added or replaced while still retaining the intended function. Therefore, in addition to the disclosed sequence of amino acids, amino acid sequences having a sequence identity of at least 85%, at least 90%, at least 95%, at least 97%, at least 98% or at least 99% at the amino acid sequence as disclosed are within the scope of the present invention.

The detection reagent of the invention may carry at least 4 and up to 200, preferable between 18 and 50, and more preferable between 25 and 45 polypeptides X; i.e. m in formulas (I) and (III) is between 4 and 200, 18-50 or 25-45.

Detection Moiety D

The detection moiety D of the detection reagent according to the invention formula (I) may be any moiety possessing a property or function which can be used for direct and indirect detection purposes like those selected from the group consisting of chromophore moiety, fluorescent moiety, phosphorescent moiety, luminescent moiety, light absorbing moiety, radioactive moiety and magnetic particles.

Preferable, detection moiety D is a fluorochrome or a magnetic particle. It should be noted that detection moieties D may comprise one or more subunits which are detectable by themselves, for example so called tandem dyes. In the present invention, such assembly of subunits are referred to a single detection moiety D.

Suitable fluorescent moieties are those known from the art of immunofluorescence technologies, e.g. flow cytometry or fluorescence microscopy. In these embodiments of the invention, the target cells labeled with the reagent are detected by exciting the detection moiety D and detecting the resulting emission.

Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metalloorganic complexes, such as Ru, Eu, Pt complexes.

In a variant of the invention, the detection moiety D, especially a fluorochrome can be destroyed by oxidation in photo- or chemical bleaching procedures (U.S. Pat. No. 7,741,045 B2, EP 0810 428 B1 or DE10143757) such that the fluorescence is quenched.

The magnetic particles used as detection moiety D are preferable nano- to microscale magnetic particle, also known in the art as magnetic bead. The mean diameter of the beads can range from 10 nm to 10 µm. Biocompatible magnetic particles are commercially available and consist of, for example, forms of magnetic iron oxide coated by a shell of dextran molecules or silica. The solid support may also be polymers containing magnetic materials. Suitable particles are commercial available from Miltenyi Biotec B.V. & Co. KG, Germany under the trade name "MicroBeads" and "MACSiBeads".

Spacer S

In the method of the invention, a compound according to general formula (II) is used as spacer S

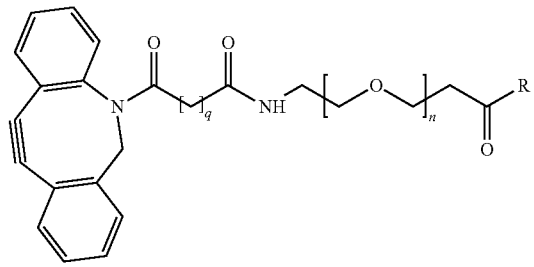

(II)

wherein R is a leaving group, q=1 to 5, and n=4 to 200

A plurality of S unit react with a detection moiety and form thereby a modified detection moiety $S_p$-D; i.e. p S units are coupled to one detection moiety D. Due to the azadibenzocyclooctyne moiety, coupling with the polypeptide X can be achieved in a strain-promoted azide-alkyne cycloaddition reaction.

Cell Detection Methods

A further object of the invention is a method for detecting cells expressing an antigen binding domain of a chimeric antigen receptor (CAR), wherein a detection reagent as disclosed is provided to a sample of cells and the cells having an antigen binding domain of a chimeric antigen receptor (CAR) binding the detection reagent are detected via the detection moiety of the detection reagent.

The cells recognizing the conjugate can be detected via detection moiety D i.e. any method that detects moieties selected from the group consisting of chromophore moiety, fluorescent moiety, phosphorescent moiety, luminescent moiety, light absorbing moiety, radioactive moiety, and chemically detectable moieties like haptens, e.g. biotin, avidin, streptavidin and derivates thereof or magnetic particles.

Preferable, the cells are detected by fluorescence emission (i.e. D is a fluorescent moiety) or by immobilizing in a magnetic field (i.e. D is a magnetic particle)

In a preferred variant of the invention, the detection moiety D is a fluorescent moiety. Target cells labeled with fluorochrome-conjugate are detected by exciting the fluorescent moiety and analyzing the resulting fluorescence signal. The wavelength of the excitation is usually selected according to the absorption maximum of the fluorescent moiety and provided by LASER or LED sources as known in the art. If several different detection moieties are used for multiple color/parameter detection, care should be taken to select fluorescent moieties having not overlapping absorption spectra, at least not overlapping absorption maxima. In case of fluorescent moieties as detection moiety the targets may be detected, e.g., under a fluorescence microscope, in a flow cytometer, a spectrofluorometer, or a fluorescence scanner. Light emitted by chemiluminescence can be detected by similar instrumentation omitting the excitation.

Use of the Method

The method of the invention can be used for various applications in research, diagnostics, quality control, cell therapy and immunomonitoring In a first variant of the invention, biological specimens like cells are detected for counting purposes i.e. to establish the amount or determine the frequency of cells from a sample having a certain set of antigens recognized by the antigen binding domain of a chimeric antigen receptor of a cell.

In a second variant, one or more populations of CAR cells are detected from a cell sample and separated as target cells from the non-detected cells. This variant may be used for purification of target cells, for example, in clinical research, diagnostics, and immunotherapy.

Suitable for such separations are especially flow sorters, e.g., FACS or MEMS-based cell sorter systems, for example as disclosed in EP14187215.0 or EP14187214.3, or magnetic separation systems, e.g. MACS.

In a third variant of the method according to the invention, the detection reagent is enzymatically cleaved thereby removing the detection moiety D from the detected cell. In an alternative method, after detection the detection moiety D is subjected to photo- and/or chemical bleaching. Both variants result in unstained cells which may be again provided with detection reagent for cell detection. Such repeated staining and destaining processes can be used to image different parts or cell structures of cells or tissue.

In a further embodiment of the invention, the CAR cells detected by the invention is for use in treatment of cancer in a subject suffering from cancer. Immune cells, e.g. T cells of a subject are isolated. The subject may suffer from said cancer or may be a healthy subject. These cells are genetically modified in vitro to express the CAR of the invention. These engineered cells may be expanded in vitro. In a cellular therapy these engineered cells are infused to a recipient in need thereof. These cells may be a pharmaceutical composition. The infused cells may be able to kill (or at least stop growth of) cancerous cells expressing the antigen, which is recognized by the antigen binding domain of the CAR of the invention in the recipient. The recipient may be the same subject from which the cells were obtained (autologous cell therapy) or may be from another subject of the same species (allogeneic cell therapy).

EXAMPLES

Synthesis of CD20 CAR Detection Reagents

A suspension of R-phycoerythrin (PE) in ammonium sulfate buffer is centrifuged for 15 min at 16060× g. The supernatant is discarded and PE dispersed in the same volume of 10 mM phosphate buffered saline (PBS) containing 5 mM ethylenediaminetetraacetic acid (EDTA), 137 mM NaCl and 2.7 mM KCl at pH 7.5 (=buffer). PE is dialyzed against the buffer overnight using a membrane with molecular weight cut-off (MWCO) of 6-8 kDa.

DBCO-PEGn-active ester (e.g. NHS, TFP, SDP) is dissolved in dry dimethyl sulfoxide (DMSO) at 10 mg/mL. 10 vol % of 0.5 M sodium bicarbonate is added to the PE solution. The required amount of DBCO-PEGn-active ester (e.g. 60 equivalent compared to PE) is added to PE and incubated under gentle shaking at room temperature in the dark for 2 h. The DBCO-conjugated PE is purified by centrifugal filtration using an appropriate MWCO filter unit and washed with buffer thrice.

The azido-functional CD20 peptide is dissolved at 500 nmol/mL in buffer. The required amount of peptide (e.g. 60 equivalent to PE) is added to the DBCO-conjugated PE and incubated under gentle shaking at room temperature in the dark for 16 h. The peptide-conjugated PE is purified by size exclusion chromatography (SEC) using a HiLoad 16/600 Superdex 200 prep grade column and PBS as eluent to remove free peptide and any high molecular weight species despite the target compound. The target fractions are combined and concentrated by centrifugal filtration using an appropriate MWCO filter unit.

The final CD20-PE conjugate is filled in buffer containing stabilizer and 0.05% sodium azide.

Analysis of Number of Peptide Per PE

The approximate number of peptides per PE is evaluated by analytical SEC. Therefore, the molar masses of the peptide-conjugated PE and unmodified PE are estimated based on a calibration curve of protein standards with known molar masses. A correction factor is determined for the estimated molar mass of PE versus its theoretical molar mass. This factor is multiplied with the estimated molar masses of the peptide-conjugated PE samples. Then, the difference of peptide-PE conjugate versus PE is divided by the molar masses of the peptide and PEG-linker minus the leaving group.

Figure 4:
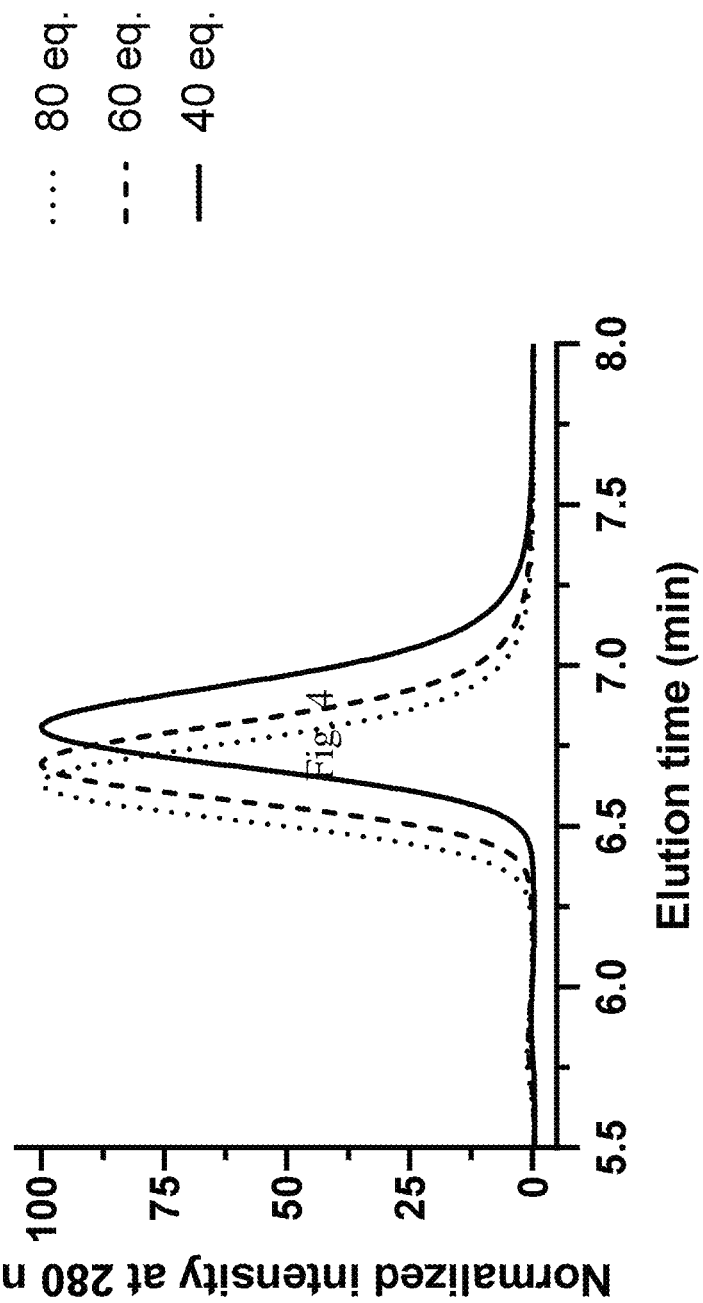
FIG. 4 shows size exclusion chromatograms of CD20-DBCO-PEG4-PE conjugates prepared with varying amounts of CD20 peptide and DBCO-PEG4-NHS added to PE.

FIG. 4 shows size exclusion chromatograms of CD20-DBCO-PEG4-PE conjugates prepared with varying amounts of CD20 peptide and DBCO-PEG4-NHS added to PE.

Figure 5:
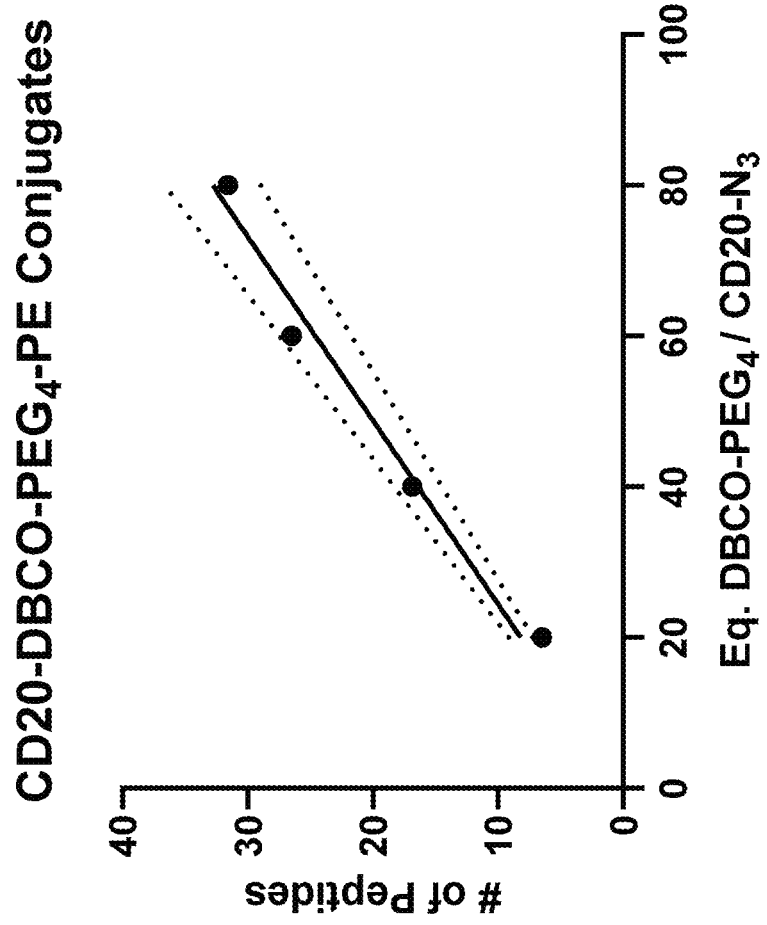
FIG. 5 shows the number of peptides per PE achieved with different amounts of DBCO-PEG4-NHS and CD20 peptide compared to PE employed in the conjugation.

FIG. 5 shows the number of peptides per PE achieved with different amounts of DBCO-PEG4-NHS and CD20 peptide compared to PE employed in the conjugation. Solid line represents a linear fit and dotted lines indicate the 95% confidence interval.

Generation CD2019 CAR-Transduced T Cells

Human Pan T cells were activated with MACS GMP TransAct kit (Miltenyi Biotec according to the manufacturers recommendations, transduced with the CD2019 CAR encoding lentiviral vector, and expanded in TexMACS medium supplemented with 3% AB serum, 10 ng/mL recombinant human IL-7, and 10 ng/mL recombinant human IL-15 at 37° C. and 5% $CO_2$ until day 14. The cells were harvested and centrifuged at 300× g for 10 minutes. The supernatant was aspirated and the cells were resuspended with 2×10E07 T cells per 1 mL PBS/EDTA/BSA (P/E/B).

Staining CD2019 CAR-Transduced T Cells

Detection of the CD20 CAR target on the CD2019 CAR-transduced T cells was done for each sample with 1×10E06 T cells in a total volume of 100 µL including P/E/B and the indicated reagents. For the detection of the CD20 CAR target different amounts of CD20 CAR detection reagent PE (0.1-2 µg/mL on cells), 10 µL 7-AAD, and 2 µL CD4-Viogreen and 2 µL CD8-APC-Vio770 were added to the cells and incubated for 10 minutes at RT. 1 mL of P/E/B was added and the cells were centrifuged at 300× g for 5 minutes. The supernatant was aspirated and the cells were resuspended with 500 µL P/E/B. For the negative controls the cells were stained in 100 µL including 10 µL 7-AAD, and 2 µL CD4-Viogreen and 2 µL CD8-APC-Vio770 and incubated for 10 minutes at RT. 1 mL of P/E/B was added and the cells were centrifuged at 300× g for 5 minutes. The supernatant was aspirated and the cells were resuspended with 500 µL P/E/B. The cell acquisition was performed on a MACSQuant Analyzer 10.

Figure 6:
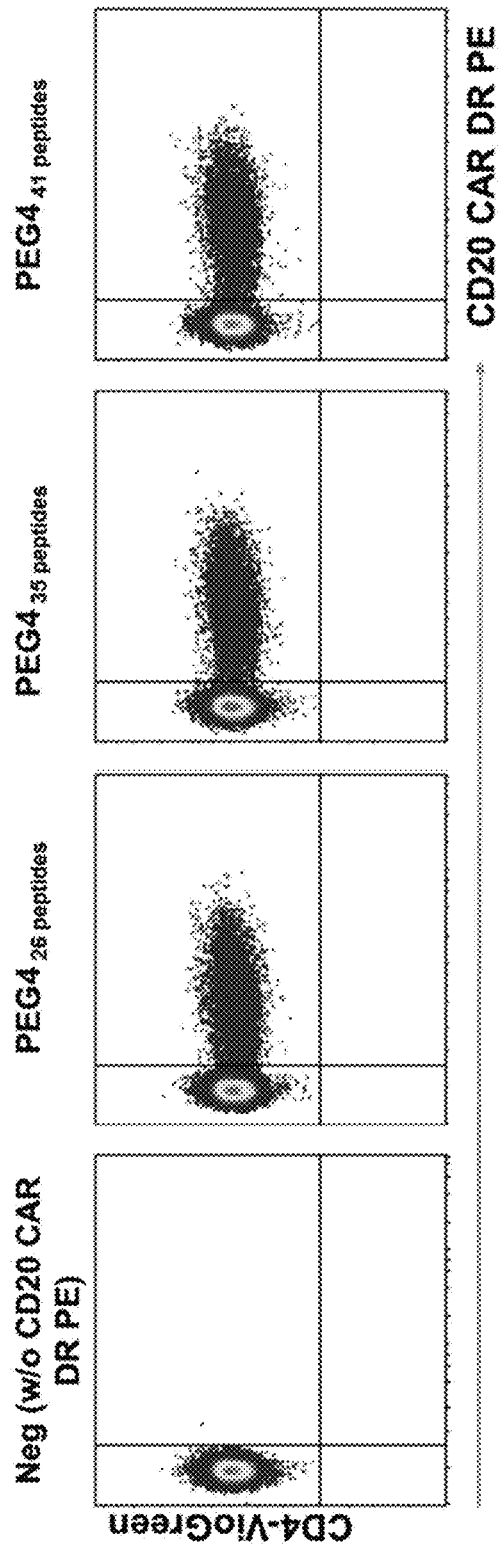
FIG. 6 shows the influence of multimerization on staining performance

FIG. 6 shows the influence of multimerization on staining performance: Flow cytometric raw data of the comparison of the CD20-DBCO-PEG4-PE conjugates prepared with varying amounts of peptide and linker added to PE for cell surface staining on CD2019 CAR-transduced T cells. As negative control CD20 CAR DR PE was left out. The plots show from left to right the negative control, the CD20-DBCO-PEG4-PE conjugates with increasing numbers of CD20 peptide (26, 35 and 41). On the Y-axis the CD4 staining is shown and on the X-axis the CD20 CAR DR PE staining In all plots viable CD4+ T cells are displayed.

Figure 7:
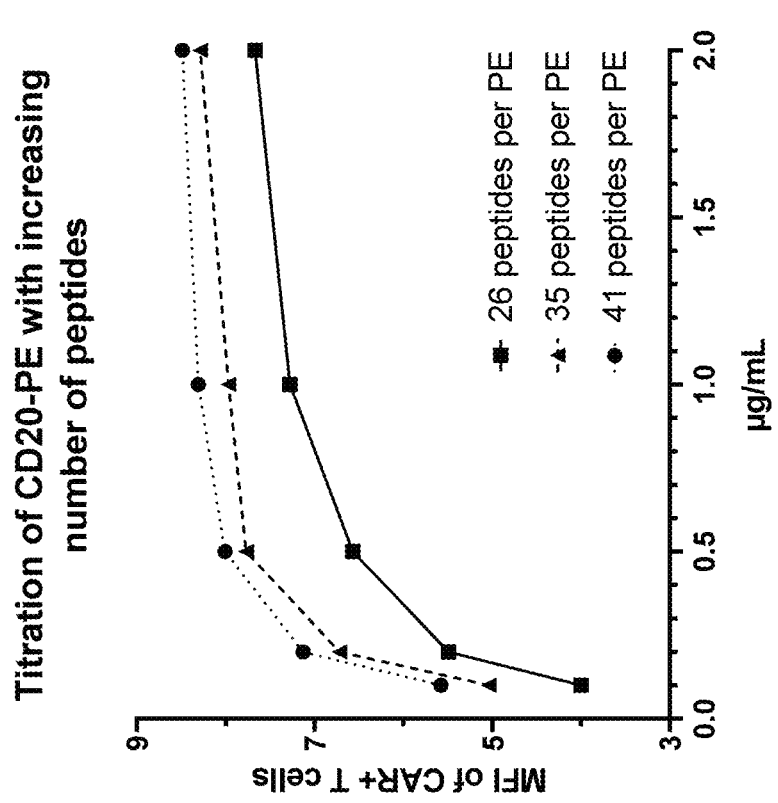
FIG. 7 shows the titration curves of samples CD20-DBCO-PEG4-PE detection reagents with increasing number of coupled peptides

FIG. 7 shows the titration curves of samples CD20-DBCO-PEG4-PE detection reagents with increasing number of coupled peptides (26, 35, 41).

Staining on Lysed Whole Blood from Healthy Donors

Background staining of the CD20 CAR detection reagent PE was done on lysed whole blood. For each sample 600 μL EDTA-whole blood from a healthy donor were added to 12 mL 1×RBC lysis solution and mixed manually and incubated for 15-20 minutes at RT until red blood lysis was completed. The cells were centrifuged at 300× g for 10 minutes. The supernatant was aspirated and the cells were resuspended in 100 μL staining mix containing 2 μL CD3-FITC, 2 μL CD4-VioGreen, 2 μL CD8-APC-Vio770, 2 μL CD45RA-VioBlue, 2 μL CD45RO-APC, 2 μL CD62L-PE-Vio770, 10 μL 7-AAD, 2 μL CD15-PerCP-Vio700, 2 μL CD14-PerCP-Vio700, and 2 μL CD20 CAR DR PE. In the negative control the CD20 CAR detection reagent PE was left out. The cells were mixed well and incubated for 10 min at RT. 1 mL of P/E/B was added and the cells were centrifuged at 300× g for 5 minutes. The supernatant was aspirated and the cells were resuspended with 500 μL P/E/B. The cell acquisition was performed on a MACSQuant Analyzer 10.

Figure 8:
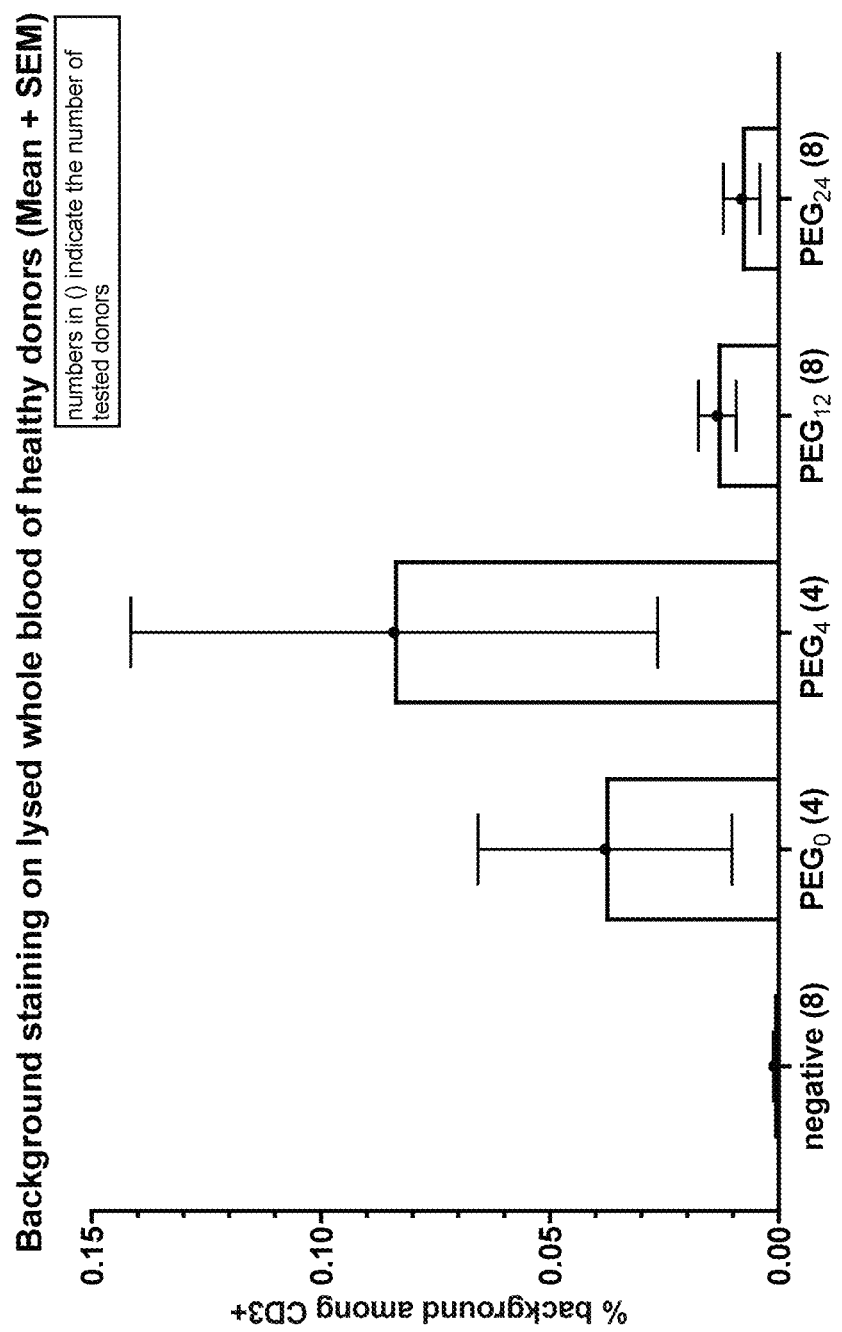
FIG. 8 shows the influence of the length of the PEG spacer between DBCO-coupled CD20-PE conjugates

FIG. 8 shows the influence of the length of the PEG spacer between DBCO-coupled CD20-PE conjugates: Flow cytometric raw data of the comparison of the CD20-DBCO-PEG-PE conjugates prepared with varying PEG spacer length for cell surface staining on lysed whole blood. As negative control CD20 CAR DR PE was left out. The plots show from left to right the negative control, the CD20-DBCO-PEG-PE conjugates with increasing PEG length (0, 12, 24). In all plots viable CD3+ T cells are displayed.

It was found that the brightness of the polypeptide-detection moiety conjugates in flow cytometry assays increased with increasing number of polypeptides per detection moiety (=multimerization effect). Higher brightness aids the detection of CAR cells in patient blood samples, where CAR cells are expected to be present only in low frequencies (between 0.01-0.5%).

For the same reason, i.e. distinguishing of low frequency CAR cells in patient whole blood samples, the background staining should be as low as possible. With increasing PEG length of the spacer the background could be reduced. Nevertheless too long PEG chains can be detrimental to the brightness of the conjugates, hence a PEG length between 10-20 repeating units was found to give a good compromise between high brightness and low background.

What is claimed is:

1. A method for preparing a detection reagent for CAR expressing cells according to general formula (I)

$(X-S)_m-D$     (I)

wherein D is a detection moiety, S a spacer unit, m=4-200 and X is a polypeptide comprising 10 to 80 amino acids and a $N_3$ group wherein X binds to the antigen binding domain of a chimeric antigen receptor of a cell, characterized in reacting p detection moieties D with a spacer S according to general formula (II)

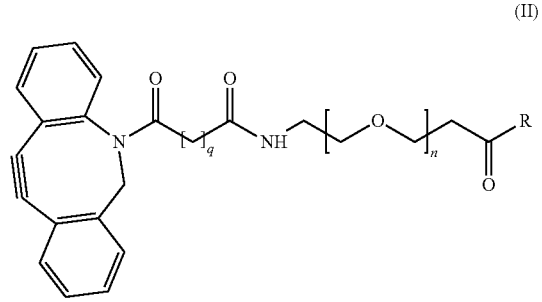

(II)

wherein R is a leaving group, q=1 to 5, and n=4 to 200 and p is 4-250;

thereby forming modified detection moiety $S_p$-D and reacting the modified detection moiety $S_p$-D with a plurality of polypeptides X to yield (X-S) m-D.

2. The method according to claim 1, characterized in that the leaving group R is selected from the group consisting of succinimidyl ester, tertafluorophenyl ester, sulfodicholorphenol ester, hydroxybenzotriazole ester and acyl chloride.

3. The method according to claim 1, characterized in that the polypeptide X is an extracellular sequence of CD20.

4. The method according to claim 1, characterized in that polypeptide X has a sequence of amino acids of CEPANPSEKNSPSTQYC (SEQ ID NO: 1.

5. The method according to claim 1, characterized in that polypeptide amino acids of X has the sequence of NIYN-CEPANPSEKNSPSTQYCYSIQ (SEQ ID NO: 2.

6. The method according to claim 1, characterized in that polypeptide X comprises at least two amino acids which are connected by at least one disulfide group.

7. The method according to claim 1, characterized in that the detection moiety D is selected from the group consisting of chromophore moiety, fluorescent moiety, phosphorescent moiety, luminescent moiety, light absorbing moiety, radioactive moiety, chemically detectable moieties and magnetic particles.

8. The method for detecting cells expressing an antigen binding domain of a chimeric antigen receptor (CAR), characterized in that a detection reagent obtained with the method according to claim 1 is provided to a sample of cells and the cells having an antigen binding domain of a chimeric antigen receptor (CAR) binding the detection reagent are detected via the detection moiety of the detection reagent.

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Homo sapiens

<400> SEQUENCE: 1

Cys Glu Pro Ala Asn Pro Ser Glu Lys Asn Ser Pro Ser Thr Gln Tyr
1               5                   10                  15

Cys

<210> SEQ ID NO 2
<211> LENGTH: 25
<212> TYPE: PRT
<213> ORGANISM: Homo sapiens

<400> SEQUENCE: 2

Asn Ile Tyr Asn Cys Glu Pro Ala Asn Pro Ser Glu Lys Asn Ser Pro
1               5                   10                  15

Ser Thr Gln Tyr Cys Tyr Ser Ile Gln
            20                  25

<210> SEQ ID NO 3
<211> LENGTH: 5
<212> TYPE: PRT
<213> ORGANISM: Homo sapiens

<400> SEQUENCE: 3

Gly Gly Gly Ser Lys
1               5

<210> SEQ ID NO 4
<211> LENGTH: 30
<212> TYPE: PRT
<213> ORGANISM: Homo sapiens

<400> SEQUENCE: 4
```

-continued

```
Asn Ile Tyr Asn Cys Glu Pro Ala Asn Pro Ser Glu Lys Asn Ser Pro
1               5                   10                  15

Ser Thr Gln Tyr Cys Tyr Ser Ile Gln Gly Gly Gly Ser Lys
            20                  25                  30
```